United States Patent [19]

Barner et al.

[11] Patent Number: 5,034,546
[45] Date of Patent: Jul. 23, 1991

[54] NOVEL VITAMIN E INTERMEDIATES AND A PROCESS FOR THEIR MANUFACTURE AND CONVERSION INTO VITAMIN E

[75] Inventors: Richard Barner, Witterswil; Josef Hübscher, Nunningen, both of Switzerland

[73] Assignee: Hoffmann-La Roche Inc., Nutley, N.J.

[21] Appl. No.: 594,913

[22] Filed: Oct. 9, 1990

Related U.S. Application Data

[62] Division of Ser. No. 341,889, Apr. 24, 1989, Pat. No. 4,996,375, which is a division of Ser. No. 119,879, Nov. 12, 1987, Pat. No. 4,851,585.

[30] Foreign Application Priority Data

Nov. 28, 1986 [CH] Switzerland ............... 4772/86
Sep. 29, 1987 [CH] Switzerland ............... 3809/87

[51] Int. Cl.$^5$ ................................. C07D 303/00
[52] U.S. Cl. ................... 549/512; 549/554; 549/563
[58] Field of Search ............... 549/512, 554, 563

[56] References Cited

U.S. PATENT DOCUMENTS

| | | | |
|---|---|---|---|
| 4,559,407 | 12/1985 | Barner et al. | 549/548 |
| 4,582,919 | 4/1986 | Barner et al. | 549/554 |
| 4,808,736 | 2/1989 | Barner et al. | 549/408 |
| 4,851,585 | 7/1989 | Barner et al. | 549/554 |

FOREIGN PATENT DOCUMENTS

| | | | |
|---|---|---|---|
| 0254086 | 1/1988 | European Pat. Off. | 549/554 |
| 2300261 | 7/1973 | Fed. Rep. of Germany. | |
| 0163372 | 10/1982 | Japan. | |
| 0077873 | 5/1983 | Japan. | |

OTHER PUBLICATIONS

Meister et al., *Liebigs Ann. Chemie*, pp. 913–921 (1983).

*Primary Examiner*—C. Warren Ivy
*Assistant Examiner*—Amelia A. Owens
*Attorney, Agent, or Firm*—George M. Gould; Bernard S. Leon; William H. Epstein

[57] ABSTRACT

Novel methyl carbinol derivatives of Vitamin E and a method for their manufacture.

4 Claims, No Drawings

NOVEL VITAMIN E INTERMEDIATES AND A PROCESS FOR THEIR MANUFACTURE AND CONVERSION INTO VITAMIN E

This is a division of application Ser. No. 341,889, filed Apr. 24, 1989, now U.S. Pat. No. 4,996,375, which in turn is a divisional application of Ser. No. 119,879, filed Nov. 12, 1987, now U.S. Pat. No. 4,851,585.

BACKGROUND OF THE INVENTION

The present invention is concerned with a novel process for the manufacture of tert. methylcarbinol derivatives, which are suitable as intermediates for the manufacture of d-α-tocopherol (natural vitamin E), and with a process for the manufacture of d-α-tocopherol itself. The invention is also concerned with novel intermediates in this process.

Several processes for the manufacture of natural vitamin E are known, but they are only of limited interest from the industrial point of view. Accordingly, natural vitamin E has hitherto been extracted almost exclusively from natural sources.

There accordingly exists a need for an industrially realizable process in accordance with which natural vitamin E can be obtained in good yield and with high optical purity. This is now possible by means of the process in accordance with the invention.

SUMMARY OF THE INVENTION

The instant invention comprises a process for the manufacture of tert.methylcarbinol derivatives which are suitable as intermediates for the manufacture of d-α-tocopherol.

The instant invention also comprises a process for the manufacture of d-α-tocopherol.

The instant invention also comprises the novel intermediates in the manufacture of d-α-tocopherol.

DETAILED DESCRIPTION

This process comprises reacting a compound of the general formula

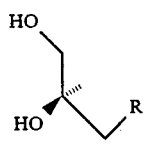
I wherein R represents a leaving group,
with a metal-organic compound of the general formula

II wherein $R^1$ represents an optionally substituted metal atom and $R^2$ signifies a residue of the formula

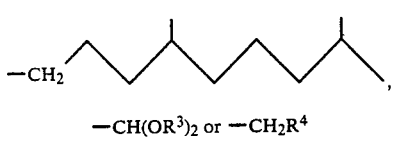

$-CH(OR^3)_2$ or $-CH_2R^4$ in which $R^3$ represents lower alkyl and $R^4$ represents halogen or an ether group.
and, if desired, converting a thus-obtained compound of the formula

III wherein $R^2$ has the above significance, into a compound of the general formula

IV wherein R and $R^2$ have the above significance,
if desired, converting a thus-obtained compound of general formula IV into an epoxide of the formula

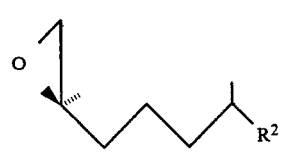
V wherein $R^2$ has the above significance,
if desired, reacting an epoxide of formula V with a compound of the general formula

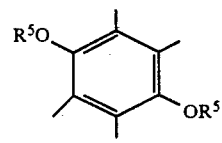
VI wherein $R^5$ represents an ether protecting group or one equivalent of an alkali metal or alkaline earth metal, and, if desired, converting a thus-obtained compound of the general formula

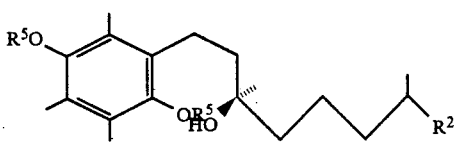
VII wherein $R^5$ has the above significance,
into d-α-tocopherol.

The term "leaving group" signifies in the scope of the present invention not only halogen such chlorine, bromine or iodine, but also sulphonic acid ester such as tosylate or mesylate as well as carboxylic acid ester such as acetate, benzoate and the like.

As metal atoms there come into consideration in the scope of the present invention the metals which are usually used for metal-organic coupling reactions, such as, for example, alkali metals or alkaline earth metals such as lithium, sodium, potassium, magnesium, as well as transition metals such as copper, titanium, zinc, mercury and the like, with magnesium being preferred. As substituents on the metal atom there come into consideration, in particular, halogen such as chlorine, bromine or iodine as well as lower alkoxy groups with 1 to 6 carbon atoms.

The term "lower alkyl" signifies in the scope of the present invention alkyl groups with 1 to 6 carbon atoms, which can be straight-chain or branched, such as, for example, methyl, ethyl, propyl, butyl, pentyl, hexyl etc. The term "lower alkoxy" signifies groups in which the alkyl residue has the foregoing significance. The term "halogen" signifies, in particular, fluorine, chlorine and bromine, with chlorine and bromine being preferred.

The term "ether protecting group" signifies in the scope of the present invention not only groups which are cleavable by hydrolysis such as, for example, the silyl group or alkoxymethyl groups, for example the methoxymethyl group, or also the tetrahydropyranyl group, but also groups which are cleavable oxidatively such as, for example, $C_1$-$C_6$-alkyl ether groups. Alternatively, the protection of the phenolic hydroxyl groups can also be achieved by an appropriate metal salt grouping, namely by an alkali metal salt or alkaline earth metal salt. Sodium, lithium and potassium are preferred. Furthermore, the notation "▼" signifies that the corresponding residue is situated above the plane of the molecule, while the notation "||||" signifies that the corresponding residue is situated below the plane of the molecule.

The reaction of a compound of general formula I with a compound of general formula II is conveniently effected by firstly reacting a compound of formula I in an inert organic solvent with an alkali metal hydride or alkaline earth metal hydride until the hydrogen evolution has finished and subsequently adding a compound of formula II.

As alkali metal hydrides or alkaline earth metal hydrides there can be used in the scope of the present invention especially lithium, sodium or potassium hydride or calcium hydride. The temperature and the pressure are of no critical significance in this reaction. The reaction is preferably effected at room temperature and normal pressure.

The conversion of a compound of general formula III into a compound of general formula IV can be effected in a manner known per se. This conversion is conveniently effected by reaction with acid halides or imidazolides in inert organic solvents, preferably with the addition of an organic base such tert. amines, e.g. pyridine, triethylamine etc.

The conversion of a compound of general formula IV into to an epoxide of general formula V can be effected in a manner known per se, i.e. by treatment with a base. Both inorganic bases and organic bases are suitable for use as bases. However, inorganic bases such as, in particular, sodium hydroxide or potassium hydroxide or also sodium hydride or calcium hydride and the like are preferred.

The reaction of an epoxide of general formula V with a compound of general formula VI is conveniently effected either by reacting a compound of formula VI. after the addition of a suitable alkali alkyl or alkaline earth alkyl compound, in an inert organic solvent with the epoxide or heating a compound of general formula VI in an inert organic solvent with the epoxide in the presence of an alkali metal hydride or alkaline earth metal hydride and a phase transfer catalyst, conveniently to a temperature of about 60° C. to about the reflux temperature of the reaction mixture and, if desired, under pressure.

As the inert organic solvent there can be used in the scope of the present invention the solvents which are usually used in metal-organic reactions. Examples of such solvents are ethers, especially cyclic ethers such as tetrahydrofuran or dioxan or also mixtures of these ethers with aliphatic hydrocarbons such as, in particular, pentane, hexane and the like.

The phase transfer catalysts which are required in the scope of the present invention are the usually used known phase transfer catalysts such as e.g. quaternary ammonium salts, crown ethers or also polyethers and the like. As alkali alkyl or alkaline earth alkyl compounds there come into consideration in the scope of the present invention e.g. tert.butyllithium, $C_1$-$C_6$-alkylpotassium, $C_1$-$C_6$-alkylsodium, Grignard compounds and the like.

The compounds of general formula VII in which $R^2$ represents the residue of the formula

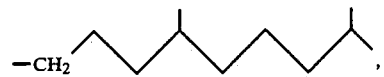

which are obtained according to the process in accordance with the invention, are known and can be converted into d-α-tocopherol in a known manner.

On the other hand, those compounds of formula VII in which $R^2$ signifies a residue of the formula —CH-$(OR^3)_2$ or —$CH_2R^4$ are novel and are also an object of the present invention. The conversion of such a compound into a compound of formula VII in which $R^2$ represents the residue

can be effected in a manner known per se, e.g. by reaction with a phosphonium salt of the formula

wherein $R^6$ represents a phenyl residue,
under the conditions which are usual for Wittig reactions or also for other metal-organic reactions. Alternatively, the chromane ring in a compound of formula VII in which $R^2$ represents a residue of the formula —CH-$(OR^3)_2$ or —$CH_2R^4$ can firstly be closed in a manner known per se, e.g. by acidic hydrolysis or by oxidation and subsequent reductive cyclization. Thereupon, the side-chain in a thus-obtained compound can be lengthened in analogy to the foregoing.

The compounds of formulae I and II which are used as starting materials in the process in accordance with the invention are known compounds or analogues of known compounds which can be prepared in an analogous manner to the preparation of the known compounds.

The present invention will be further described in connection with the following examples which are set forth for the purpose of illustration only.

EXAMPLE 1

367 mg (3 mmol) of (2S)-3-chloro-2-methyl-1,2-propanediol were dissolved in 5 ml of dry tetrayhydrofuran and left to react at room temperature with 100 mg (7.2 mmol) of sodium hydride (55-60%) until the evolution of gas had finished. 350 mg of potassium tert.-butylate were added to the resulting thick suspension. Thereupon, 2.9 mmol of (3RS,7RS)-3,7,11-trimethyldodecylmagnesium bromide were added and the mixture was stirred at room temperature for 16 hours. 50 ml of water were subsequently added and the mixture was extracted with ether. The organic phases were dried over sodium sulphate and concentrated. There was obtained 0.81 g (96%) of (2R,6RS,10RS)-2,6,10,14-tetramethyl-1,2-pentadecanediol with $[\alpha]_D^{20} = +1.35°$ (c=1.5% in CHCl$_3$).

The (2S)-3-chloro-2-methyl-1,2-propanediol used as the starting material was prepared as follows:

7.9 ml (26 mmol) of tetraisopropyl orthotitanate, 150 mg (2.5 mmol) of calcium hydride, 150 mg (2.5 mmol) of silica gel and 5 ml (30 mmol) of dibutyl L-tartrate were left to stand at $-18°$ C. for 10 minutes in 150 ml of methylene chloride. Then, 1.6 ml (25 mmol) of beta-methallyl alcohol and 7 ml (50 mmol) of cumene hydroperoxide (66% in cumene) were added dropwise and the mixture was left to stand at $-18°$ C. for 16 hours. Thereupon. 300 ml of diethyl ether and 50 ml (0.35 mol) of sodium hydroxide solution (28%) were added and the mixture was stirred at room temperature for 1.5 hours. The mixture was then extracted with ether, the organic phases were treated with 20.3 g (0.1 mol) of magnesium chloride and stirred at room temperature for 16 hours. The mixture was subsequently filtered, the filtrate was concentrated and cumene and cumene alcohol were distilled off with steam. The residue was concentrated and there were obtained 2.47 g of (2S)-3-chloro-2-methyl-1,2-propanediol as a colourless oil with $[\alpha]_D^{20} = +5.4°$ (c=3% in CHCl$_3$) and an optical purity of above 98% (e.e.) according to gas-chromatographical methods (Mosher derivative). In an analogous way, compound III with R$^2$=CH(OCH$_3$)$_2$ or R$^2$=CH$_2$-O-CH$_2$-Ph can be obtained by using the corresponding Grignard-reagent II (R$^1$=MgBr).

EXAMPLE 2

0.81 g (2.8 mmol) of (2R,6RS,10RS)-2,6,10,14-tetramethyl-1,2-pentadecanediol and 540 mg (2.9 mmol) of tosyl chloride were left to react at room temperature for 16 hours in 2 ml of pyridine. The mixture was then treated with 50 ml of 1N hydrochloric acid and extracted three times with 50 ml of diethyl ether each time. The organic phases were dried over sodium sulphate and concentrated. There were obtained 1.22 g (99%) of (2R,6RS,10RS)-1-tosyloxy-2,6,10,14-tetramethyl-3-pentadecanol with $[\alpha]_D^{20} = -1.48°$ (c=2% in CHCl$_3$).

EXAMPLE 3

760 mg (2.9 mmol) of 2,5-di-(methoxymethoxy)-1,3,4,6-tetramethylbenzene were dissolved in 20 ml of tetrahydrofuran, treated at room temperature with 330 mg of potassium tert.butylate and subsequently with 2 ml (3.2 mmol) of n-butyllithium and left to react for 1 hour. The mixture was then left to react at room temperature for 16 hours with (2R,6RS,10RS)-1,2-epoxy-2,6,10,14-tetramethylpentadecane, prepared from 1.22 g of (2R,6RS,10RS)-1-tosyloxy-2,6,10,14-tetramethyl-3-pentadecanol and 500 mg (3.1 mmol) of sodium hydride in 30 ml of tetrahydrofuran. Thereupon, 10 ml of HBr (30%) in 50 ml of methanol were added and the mixture was left to stand for 24 hours. Subsequently, methanol was added and the mixture was then concentrated to dryness. The residue was filtered over silica gel with toluene and there were obtained 1.1 g (88%) of (2R,4'RS,8'RS)-α-tocopherol.

EXAMPLE 4

1.52 g (3.3 mmol) of (2R,6RS,10RS)-2,6,10,14-tetramethyl-1-tosyloxy-2-pentadecanol were dissolved in 20 ml of ethanol. 2 ml of sodium hydroxide solution (50%) were then added and the mixture was stirred for 16 hours. Subsequently, 50 ml of water were added and the mixture was stirred up with HYFLO. The suspension was then filtered and washed with water. The residue was triturated with diethyl ether, dried over sodium sulphate, filtered and concentrated. There was obtained (2R,6RS,10RS)-1,2-epoxy-2,6,10,14-tetramethylpentadecane with $[\alpha]_D^{20} = -0.21°$ (c=2% in CHCl$_3$).

EXAMPLE 5

1.8 g (9 mmol) of 2,5-dimethoxy-1,3,4,6-tetramethylbenzene were dissolved in 100 ml of tetrahydrofuran, treated with 1 g (9 mmol) of potassium tert.butylate and subsequently 6 ml (9.5 mmol) of n-butyllithium (1.6 molar) were added dropwise at room temperature. Thereafter, the mixture was stirred at room temperature for 30 minutes, treated dropwise with 2.7 g (9 mmol) of (2RS,6RS,10RS)-1,2-epoxy-2,6,10,14-tetramethylpentadecane and stirred at room temperature for 16 hours. Thereupon. HYFLO and 200 ml of water were added, the mixture was then filtered and washed with water. The residue was stirred up with diethyl ether and sodium sulphate, filtered, washed with diethyl ether and concentrated. There were obtained 3.8 g of (3RS,7RS,11RS)-1-(2,5-dimethoxy-3,4,6-trimethylphenyl)-3,7,11,15-tetramethyl-3-hexadecanol.

EXAMPLE 6

10 g (66.7 mmol) of tetramethylhydroquinone are dissolved in 100 ml of dry tetrahydrofuran, 4 g (139 mmol) of sodium hydride (80% in mineral oil) are added thereto at room temperature, 45 ml of butyllithium (1.6 molar in hexane) are subsequently added dropwise and the mixture is stirred for 1 hour. 10 g (44.3 mmol) of 1,2-epoxy-2,6,10,14-tetramethylpentadecane are now added dropwise; the mixture is left to react for 12 hours while stirring. 100 ml of 1N methanolic hydrochloric acid are added and the mixture is stirred at 50° C. for 2 hours. The mixture is subsequently concentrated at 50° C. and the residue is chromatographed on silica gel with toluene, whereby there are obtained 14.9 g (75%) of α-tocopherol.

We claim:

1. The compounds of the formula

V wherein R$^2$ is

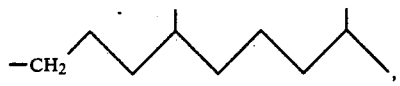
—CH(OR³)₂ or —CH₂R⁴
R³ is lower alkyl and R⁴ is halogen or forms a hydrolyzable ether group.
2. The compound of claim 1 wherein R² is
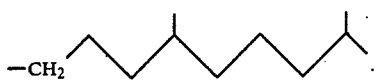
3. The compound of claim 1 wherein R² is —CH(OR³)₂.
4. The compound of claim 1 wherein R² is —CH₂R⁴.
* * * * *